United States Patent
Simonnet

(10) Patent No.: US 7,381,403 B2
(45) Date of Patent: Jun. 3, 2008

(54) FINELY DIVIDED PHOTOPROTECTIVE OIL-IN-WATER EMULSIONS COMPRISING 4,4-DIARYLBUTADIENE UV-A SUNSCREENS

(75) Inventor: Jean-Thierry Simonnet, Cachan (FR)

(73) Assignee: L'Oreal, Paris (FR)

( * ) Notice: Subject to any disclaimer, the term of this patent is extended or adjusted under 35 U.S.C. 154(b) by 647 days.

(21) Appl. No.: 10/823,715

(22) Filed: Apr. 14, 2004

(65) Prior Publication Data

US 2004/0258644 A1 Dec. 23, 2004

Related U.S. Application Data

(60) Provisional application No. 60/468,113, filed on May 6, 2003.

(30) Foreign Application Priority Data

Apr. 14, 2003 (FR) .................. 03 04648

(51) Int. Cl.
- *A61Q 17/04* (2006.01)
- *A61Q 17/00* (2006.01)
- *A61Q 19/04* (2006.01)
- *A61Q 19/00* (2006.01)
- *A61K 8/02* (2006.01)
- *A61K 8/06* (2006.01)

(52) U.S. Cl. .................. 424/59; 424/60; 424/400; 424/401

(58) Field of Classification Search .................. 424/59, 424/60, 400, 401
See application file for complete search history.

(56) References Cited

U.S. PATENT DOCUMENTS 6,126,948 A 10/2000 Simonnet et al.
6,238,649 B1 5/2001 Habeck et al.
6,436,373 B1 8/2002 Habeck et al.
2002/0035182 A1 3/2002 L'Alloret et al.
2004/0170580 A1 9/2004 Schmidt et al.

FOREIGN PATENT DOCUMENTS

| EP | 0 864 320 A1 | 9/1998 |
|----|---|---|
| EP | 0 916 335 A2 | 5/1999 |
| EP | 1 008 586 A1 | 6/2000 |
| EP | 1 025 901 A1 | 8/2000 |
| EP | 1 172 077 A1 | 1/2002 |
| FR | 2 801 210 A1 | 5/2001 |
| WO | WO 02/080878 A2 | 10/2002 |

OTHER PUBLICATIONS

French Search Report Issued in French Priority Counterpart FR 03/04648 on Jan. 9, 2004, 4 pages.
Abstract of FR 2801210, published May 5, 2001, downloaded Dec. 19, 2007 at http://v3.espacenet.com/textdoc?DB=EPODOC&IDX=FR2801210&F=0.
Abstract of EP 1025901, published Aug. 9, 2000, downloaded Dec. 19, 2007 at http://v3.espacenet.com/textdoc?DB=EPODOC&IDX=EP1025901&F=0.

*Primary Examiner*—Shelley A. Dodson
(74) *Attorney, Agent, or Firm*—Buchanan, Ingersoll & Rooney, PC

(57) ABSTRACT

UV-Photoprotective oil-in-water emulsions well suited for photoprotecting the skin, lips and/or hair against the damaging effects of UV-radiation, the oil globules of which having an average size of at most 500 nm and containing particles of at least one ionic polymer and at least one UV-radiation-screening system, such screening system comprising at least one 4,4-diarylbutadiene UV-A-screening agent.

47 Claims, No Drawings

FINELY DIVIDED PHOTOPROTECTIVE OIL-IN-WATER EMULSIONS COMPRISING 4,4-DIARYLBUTADIENE UV-A SUNSCREENS

CROSS-REFERENCE TO PRIORITY/PROVISIONAL APPLICATIONS

This application claims priority under 35 U.S.C. § 119 of FR 03/04648, filed Apr. 14, 2003, and of provisional application Ser. No. 60/468,113, filed May 6, 2003, both hereby expressly incorporated by reference and both assigned to the assignee hereof. This application is also a continuation of said '113 provisional.

BACKGROUND OF THE INVENTION

1. Technical Field of the Invention

The present invention relates to oil-in-water photoprotective emulsions in which the oil globules of the emulsion have an average diameter of at most 500 nm, containing at least particles of ionic polymer and at least one UV radiation-screening system, which screening system comprises at least one UV-A-screening agent of the 4,4-diarylbutadiene type.

2. Description of Background and/or Related and/or Prior Art

It is well known that light radiation having wavelengths of between 280 nm and 400 nm allows tanning of the human epidermis, and that rays having wavelengths of between 280 nm and 320 nm, known by the name UV-B, cause erythemas and skin burns which can hamper the development of the natural tan; this UV-B radiation must therefore be screened out.

It is also known that UV-A rays having wavelengths of between 320 nm and 400 nm, which cause tanning of the skin, are capable of inducing its impairment, in particular in the case of a sensitive skin or a skin continually exposed to solar radiation. UV-A rays cause in particular a loss of elasticity of the skin and the appearance of wrinkles which lead to premature aging. They promote the onset of the erythematous reaction or amplify this reaction in some subjects and may even be responsible for phototoxic or photoallergic reactions. It is therefore desirable to also screen out UV-A radiation.

UV-A and UV-B rays must therefore be screened out and protective cosmetic compositions for the human epidermis containing UV-A- and UV-B-screening agents currently exist.

For various reasons linked in particular to their great comfort in use and to their refreshing property, cosmetic compositions, and in particular those intended for photoprotecting the skin against UV-A and UV-B rays, called antisun/sunscreen compositions, are most often provided in the form of an emulsion of the oil-in-water type, containing an oily phase homogeneously dispersed in an aqueous phase. In these conventional emulsions, which contain emulsifying agents (or surfactants) and optional cosmetic additives, the size of the globules constituting the fatty phase is generally greater than several microns. Such emulsions may have inadequate cosmetic properties (oily feel) and physical properties (stability).

One of the major objectives of the antisun/sunscreen compositions of the O/W type known to date is to have perfect emulsion stability combined with photoprotection which is as broad as possible and improved safety. The expression stability of the emulsion is understood to mean that the dispersion remains macroscopically and microscopically (particle size) stable over a period of time of at least 30 days.

Moreover, it is observed that despite the presence of emulsifying agents (or surfactants), some of these emulsions exhibit a lack of stability over time, a lack of stability resulting in the appearance of a phenomenon of separation (phase separation) between the aqueous and oily phases of the emulsion. This instability hampers the preservation of the emulsions.

Accordingly, to avoid this undesirable phenomenon, it is often necessary to resort to so-called thickening agents, which are then introduced into the emulsion and whose primary function is to create, in the aqueous phase, a gelled matrix which serves to immobilize the globules of the fatty phase within its three-dimensional network, thus ensuring mechanical preservation of the whole emulsion. However, this addition of thickening agent limits the galenic forms which are possible, by excluding in particular very fluid compositions.

To date, it is increasingly sought to prepare fluid, in particular antisun, compositions, more especially with the aim of having easily vaporizable products which are often considered by the user as being easier to apply than creams.

Finally, to limit as much as possible the risks of intolerance, in particular of so-called "sensitive" skins, it is increasingly sought to limit as much as possible, in the manufacture of oil/water emulsions, the use of emulsifying surfactants which, through their action, can make fragile the barrier function of the epidermis.

To remedy these problems and to respond to these needs, particularly stable fine and fluid emulsions containing and stabilized by particles of ionic polymer have been developed in EP-0-864,320, the oil globules of these emulsions having an average diameter of less than 500 nanometres. These emulsions have particularly satisfactory sensory qualities (feel). These emulsions may be used for photoprotecting the skin and the hair against the effects of UV rays since they can contain UV-A screening agents and/or UV-B-screening agents.

Among the available organic UV-A-screening agents, a family of compounds which are particularly effective in the UV-A region is 1,4-benzene[di(3-methylidene-10-camphorsulfonic)] acid and its different salts, which is described in particular in FR-A-2,528,420 and FR-A-2,639,347; they are indeed capable of absorbing ultraviolet rays having wavelengths of between 280 nm and 400 nm, with absorption maxima of between 320 nm and 400 nm, in particular in the region of 345 nm.

However, the introduction of this type of UV-A-screening agent, even sometimes in low doses, into fine oil-in-water emulsions stabilized with particles of ionic polymer rapidly leads to their destabilization. This forces the formulator to use them in very low concentrations and to limit the photoprotective efficacy in particular in the UV-A domain.

It thus appears necessary to provide fine antisun/sunscreen oil-in-water emulsions based on particles of ionic polymer which are stable and which may contain organic screening agents active in UV-A of comparable efficacy to that of 1,4-benzene[di(3-methylidene-10-camphorsulfonic)] acid and its different salts without the disadvantages listed above.

SUMMARY OF THE INVENTION

It has now surprisingly and unexpectedly been determined that finely divided antisun/sunscreen oil-in-water emulsions based on particles of ionic polymer and at least one UV-A-screening agent of the 4,4-diarylbutadiene type ameliorate or avoid those disadvantages and drawbacks indicated above.

In the remainder of the present description, the expression "UV radiation-screening system" is understood to mean a UV radiation-screening agent comprising either a single organic or inorganic compound screening out UV radiation or a mixture of several organic or inorganic compounds screening out UV radiation, for example a mixture comprising a UV-A-screening agent and a UV-B-screening agent.

This discovery forms the basis of the present invention.

Thus, the present invention features oil-in-water emulsions in which the oil globules of the emulsion have an average diameter of at most 500 nm, containing at least particles of ionic polymer and at least one UV radiation-screening system, which screening system comprises at least one UV-A-screening agent of the 4,4-diarylbutadiene type.

Other characteristics, aspects and advantages of the invention will be seen from the detailed description which follows.

In the remainder of the present description, the expression "UV radiation-screening system" is understood to mean a UV radiation-screening agent comprising either a single organic or inorganic compound screening out UV radiation or a mixture of several organic or inorganic compounds screening out UV radiation, for example a mixture comprising a UV-A-screening agent and a UV-B-screening agent.

The expression "ionic polymer" is understood to mean both a homopolymer and a copolymer. The polymers are intended in particular to disperse the oily phase in the aqueous phase.

DETAILED DESCRIPTION OF BEST MODE AND SPECIFIC/PREFERRED EMBODIMENTS OF THE INVENTION

The emulsions according to the invention have in particular the advantage of being very fluid while having a very good stability, even in the absence of gelling agent.

In addition to the advantages mentioned above (fluidity, stability), the use of the polymer particles as dispersant makes it possible to carry out, in the cold state, the step of dispersing the oily phase in the aqueous phase, which is simpler and less costly than the conventional methods carried out most often in the hot state when surfactants are used. Manufacture in the cold state allows for example the introduction of heat-sensitive active agents without the risk of degradation of these active agents.

Advantageously, the emulsions of the invention are free of surfactant. Thus, because of the absence of surfactant, this emulsion has the advantage of not being irritating for particularly sensitive skins.

Moreover, the emulsion thus obtained is very fine and has particularly satisfactory sensory qualities. The average size of the globules constituting the oily phase is less than 500 nm, and it preferably ranges from 150 nm to 300 nm.

The emulsion according to the invention may be very fluid, which means that it may have a viscosity of less than 15,000 cPs (that is 15 Pa·s), more preferably still less than 5,000 cPs (that is 5 Pa·s) (measured on a Brookfield RVT model DV2 viscometer, at 0.5 rpm and with a No. 5 disc).

In general, the particles which can be used in the invention may be prepared from an ionic polymer, from a mixture of ionic polymers or from a mixture of at least one ionic polymer and at least one nonionic polymer. These polymers should be nontoxic and nonirritating for the skin. In addition, they must be dispersible in water in particulate form.

The ionic polymer may be cationic or anionic.

It is preferably an anionic polymer.

The water-dispersible anionic polymers which can be used in the invention are, for example, the polymers of isophthalic acid or of sulfoisophthalic acid, and in particular the copolymers of phthalate/sulfoisophthalate/glycol (for example diethylene glycol/phthalate/isophthalate/1,4-cyclohexanedimethanol) sold under the names "Eastman AQ polymer" (AQ35S, AQ38S, AQ55S, AQ48 Ultra) by Eastman Chemical.

These polyesters may also contain units derived from ethylene glycol, triethylene glycol and/or tetraethylene glycol and terephthalic acid such as those marketed under the names POLYCARE PS 20, POLYCARE PS30 and POLYCARE PS 32 by Rhodia.

The proportion of units derived from sulfoisophthalic acid preferably varies from 2% to 20% by weight relative to the total weight of the polymer.

The water-dispersible anionic polymers which can be used in the invention may also be among the film-forming vinyl copolymers commonly used for the preparation of cosmetic compositions, among which there may be mentioned:

(i) polyethoxylated vinyl acetate/crotonic acid copolymers such as that marketed under the name ARISTOFLEX A by HOECHST;

(ii) vinyl acetate/crotonic acid copolymers such as that marketed under the name LUVISET CA66 by BASF;

(iii) vinyl acetate/crotonic acid/vinyl neodecanoate terpolymers such as that marketed under the name RESINE 28-29-30, by NATIONAL STARCH;

(iv) N-octylacrylamide/methyl methacrylate/hydroxypropyl methacrylate/acrylic acid/tert-butylaminoethyl methacrylate copolymers such as that marketed under the name AMPHOMER by NATIONAL STARCH;

(v) methyl vinyl ether/maleic anhydride alternating copolymers monoesterified with butanol, such as that marketed under the name GANTREZ ES 425 by GAF;

(vi) acrylic acid/ethyl acrylate/N-tert-butylacrylamide terpolymers such as that marketed under the name ULTRAHOLD 8 by BASF.

As natural water-dispersible anionic polymers which can be used according to the present invention, there may be mentioned shellac resin, sandarac gum and dammars.

Shellac resin is an animal secretion composed mainly of resin and wax and is soluble in certain organic solvents. It must be under-neutralized so as not to become soluble in water.

Dammars are resins obtained from trees of the genera Damara and Shorea and generally contain 62.5% resenes (40% of solubles and 22.5% of insolubles in alcohol) and 23% of acids.

The weight-average molar mass of the water-dispersible anionic polymers of the present invention generally ranges from 1,000 to 5,000,000.

Advantageously, the particles of ionic polymer which are used according to the invention have a particle size ranging from 10 nm to 400 nm, and better still ranging from 20 nm to 200 nm according to the nature of the ionic polymer.

The particles of these polymers may be used as such or as a dispersion in water.

The ratio between the quantity of polymer particles and the quantity of oily phase ranges from 1/5 to 1/40.

In the emulsions of the invention, it is possible to use a quantity of polymer particles ranging from 0.1% to 10%, preferably from 0.5% to 5%, and better still from 1% to 2% of the total weight of the composition.

These emulsions are combined with a particular high-pressure homogenization method which makes it possible to obtain the required size. The obtaining of this size is explained by a very substantial improvement in the stability of the dispersion.

A first step entails mixing, with stirring, the aqueous phase, the oily phase and the polymer particles and, in a second step, in subjecting the mixture obtained to homogenization based on the principle of cavitation.

The mixture is first subjected to conventional stirring, for example in a homogenizer revolving at a speed of between 500 and 5,000 revolutions/min for a period of between 10 min and 60 min approximately, at a temperature of between 20° C. and 95° C. approximately.

The homogenization based on the principle of cavitation of the second step is a key step of the method according to the invention. This homogenization results from the phenomenon of cavitation created and maintained in the mixture, then in liquid form, in movement at a linear speed of at least 100 m/s.

This homogenization may be performed by the use of a high-pressure homogenizer operating at a pressure ranging from 100 to 1,000 bar approximately, and preferably from 400 to 700 bar. The principle of the use of this type of homogenizer is well known to persons skilled in the art. The procedure is carried out at room temperature by successive passes, generally from 2 to 10 passes, under a selected pressure, the mixture being brought to room temperature between each pass.

Homogenization may also be obtained under the action of ultrasound or alternatively by the use of homogenizers equipped with a rotor-stator-type head.

The 4,4-diarylbutadiene compounds in accordance with the invention are preferably selected from among those corresponding to the following formula (I):

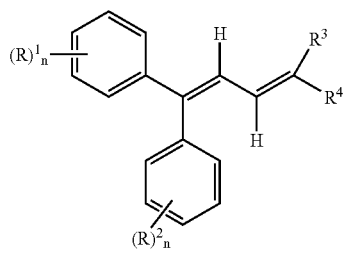
(I)

in which the diene system is of the Z,Z; Z,E; E,Z or E,E configuration or mixtures of the said configurations, and wherein:

$R^1$ and $R^2$, which may be identical or different, are each hydrogen, a $C_1$-$C_{20}$ alkyl radical, a $C_2$-$C_{10}$ alkenyl radical, a $C_1$-$C_{12}$ alkoxy radical, a $C_3$-$C_{10}$ cycloalkyl radical, a $C_3$-$C_{10}$ cycloalkenyl radical, a $C_1$-$C_{20}$ alkoxycarbonyl radical, a $C_1$-$C_{12}$ monoalkylamino radical, a $C_1$-$C_{12}$ dialkylamino radical, an aryl radical, a heteroaryl radical or a water-solubilizing substituent selected from among a carboxylate residue, a sulfonate residue or an ammonium residue;

$R^3$ is a group $COOR^5$, $COR^5$, $CONR^5R^6$, CN, O=S(—$R^5$)=O, O=S(—$OR^5$)=O, $R^7O$—P—(—$OR^8$)=O, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$C_{18}$ aryl radical, an optionally substituted $C_3$-$C_7$ heteroaryl radical;

$R^4$ is a group $COOR^6$, $COR^6$, $CONR^5R^6$, CN, O=S(—$R^6$)=O, O=S(—$OR^6$)=O, $R^7O$—P—(—$OR^8$)=O, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3C_{10}$ cycloalkenyl radical, a $C_7$-$C_{10}$ bicycloalkenyl radical, an optionally substituted $C_6$-$C_{18}$ aryl radical, an optionally substituted $C_3$-$C_7$ heteroaryl radical;

the radicals $R^5$ to $R^8$, which may be identical or different, are each hydrogen, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ bicycloalkenyl radical, a $C_7$-$C_{10}$ cycloalkenyl radical, an optionally substituted aryl radical, an optionally substituted heteroaryl radical; and n ranges from 1 to 3; with the proviso that the radicals $R^3$ to $R^8$ can together form, with the carbon atoms from which they depend, a $C_5$-$C_6$ ring which may be fused.

As $C_1$-$C_{20}$ alkyl radicals, there may be mentioned, for example: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

As $C_2$-$C_{10}$ alkenyl groups, there may be mentioned, for example: ethenyl, n-propenyl, 1-methylethenyl, n-butenyl, 1-methylpropenyl, 2-methylpropenyl, 1,1-dimethylethenyl, n-pentenyl, 1-methylbutenyl, 2-methylbutenyl, 3-methylbutenyl, 2,2-dimethylpropenyl, 1-ethylpropenyl, n-hexenyl, 1,1-dimethylpropenyl, 1,2-dimethylpropenyl, 1-methylpentenyl, 2-methylpentenyl, 3-methylpentenyl, 4-methylpentenyl, 1,1-dimethylbutenyl, 1,2-dimethylbutenyl, 1,3-dimethylbutenyl, 2,2-dimethylbutenyl, 2,3-dimethylbutenyl, 3,3-dimethylbutenyl, 1-ethylbutenyl, 2-ethylbutenyl, 1,1,2-trimethylpropenyl, 1,2,2-trimethylpropenyl, 1-ethyl-1-methylpropenyl, 1-ethyl-2-methylpropenyl, n-heptenyl, n-octenyl, n-nonenyl, n-decenyl.

As $C_1$-$C_{12}$ alkoxy radicals, there may be mentioned: methoxy, n-propoxy, 1-methylpropoxy, 1-methylethoxy, n-pentoxy, 3-methylbutoxy, 2,2-dimethylpropoxy, 1-methyl-1-ethylpropoxy, octoxy, ethoxy, n-propoxy, n-butoxy, 2-methylpropoxy, 1,1-dimethylpropoxy, hexoxy, heptoxy, 2-ethylhexoxy.

As $C_1$-$C_{20}$ alkoxycarbonyl radicals, there may be mentioned esters of $C_1$-$C_{20}$ alcohols.

As $C_1$-$C_{12}$ monoalkylamino or dialkylamino radicals, there may be mentioned those in which the alkyl radical(s) is (are) selected from among methyl, n-propyl, 2-methylpropyl, 1,1-dimethylethyl, hexyl, heptyl, 2-ethylhexyl, isopropyl, 1-methylpropyl, n-pentyl, 3-methylbutyl, 2,2-dimethylpropyl, 1-methyl-1-ethylpropyl, octyl.

As $C_3$-$C_{10}$ cycloalkyl radicals, there may be mentioned, for example: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

As $C_3$-$C_{10}$ cycloalkenyl radicals having one or more double bonds, there may be mentioned: cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctetraenyl, cyclononenyl or cyclodecenyl.

The cycloalkyl or cycloalkenyl radicals may comprise one or more substituents (preferably from 1 to 3) selected, for example, from among halogens such as chlorine, fluorine or bromine; cyano; nitro; amino; $C_1$-$C_4$ alkylamino; $C_1$-$C_4$ dialkylamino; $C_1$-$C_4$ alkyl; $C_1$-$C_4$ alkoxy; hydroxyl; they may also comprise from 1 to 3 heteroatoms such as sulfur, oxygen or nitrogen whose free valencies may be saturated with a hydrogen or a $C_1$-$C_4$ alkyl radical.

The bicycloalkyl or bicycloalkenyl groups are selected, for example, from among bicyclic terpenes such as pinane, bornane, pinene or camphor or adamantane derivatives.

The aryl groups are preferably selected from phenyl or naphthyl rings, which may comprise one or more substituents (preferably from 1 to 3) selected for example from halogen such as chlorine, fluorine or bromine; cyano; nitro; amino; $C_1$-$C_4$ alkylamino; $C_1$-$C_4$ dialkylamino; $C_1$-$C_4$ alkyl; $C_1$-$C_4$ alkoxy; hydroxyl. Phenyl, methoxyphenyl, naphthyl and thienyl are more particularly preferred.

The heteroaryl groups comprise in general one or more heteroatoms selected from among sulfur, oxygen or nitrogen.

The water-solubilizing groups are for example carboxyl and sulfoxy residues, and more particular their salts with physiologically acceptable cations such as alkali metal salts or trialkylammonium salts such as tri(hydroxyalkyl)ammonium or 2-methylpropan-1-ol-2-ammonium salts. There may also be mentioned ammonium groups such as alkylammoniums and their salified forms with physiologically acceptable anions.

The compounds of formula (I) are known per se and their structures and their syntheses are described in DE-1,9755,649, EP-916,335, EP-1,133,980 and EP-1,133,981.

By way of example of compounds of formula (I), the following are representative:

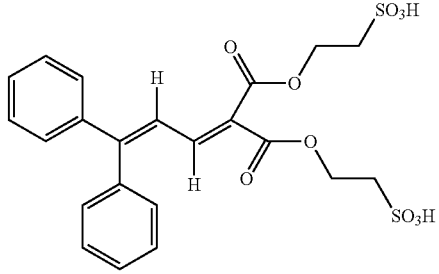
(compound a)

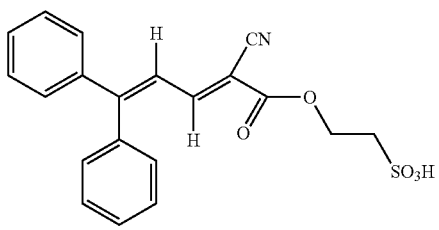
(compound b)

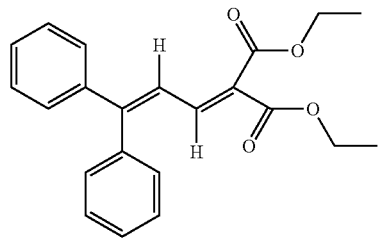
(compound c)

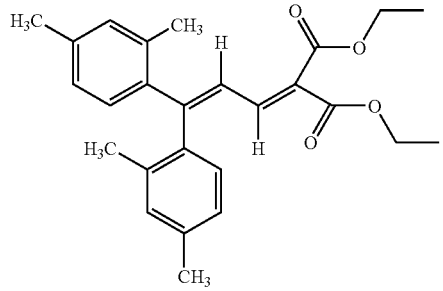
(compound d)

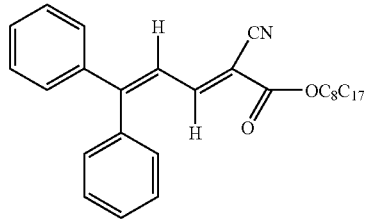
(compound e)

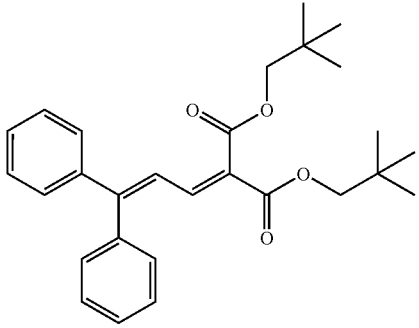
(compound f)

The preferred compounds of formula (I) are those in which:
n=1 or 2;
$R^1$ and $R^2$, which may be identical or different, are each hydrogen, a $C_1$-$C_{20}$ alkyl radical, a $C_1$-$C_{12}$ alkoxy radical, a $C_1$-$C_{12}$ monoalkylamino radical, a $C_1$-$C_{12}$ dialkylamino radical, a water-solubilizing substituent selected from among a carboxylate group, a sulfonate group or an ammonium residue;
$R^3$ is a group $COOR^5$, $COR^5$, $CONR^5R^6$, a $C_1$-$C_{20}$ alkyl radical, a $C_3$-$C_{10}$ cycloalkyl radical, a $C_3$-$C_{10}$ cycloalkenyl radical, a $C_7$-$C_{10}$ bicycloalkyl radical, optionally substituted phenyl, naphthyl or thienyl;
$R^4$ is a group $COOR^6$, $COR^6$, $CONR^5R^6$, a $C_1$-$C_{20}$ alkyl radical, a $C_3$-$C_6$ cycloalkyl radical, a $C_3$-$C_{10}$ cycloalkenyl radical, a $C_7$-$C_{10}$ bicycloalkyl radical, optionally substituted phenyl, naphthyl or thienyl; and
the radicals $R^5$ and $R^6$, which may be identical or different, are each hydrogen, a $C_1$-$C_{12}$ alkyl radical, a $C_3$-$C_{10}$ cycloalkyl radical, a $C_3$-$C_{10}$ cycloalkenyl radical, a $C_7$-$C_{10}$ bicycloalkyl radical, a $C_3$-$C_{10}$ bicycloalkenyl radical, optionally substituted phenyl or naphthyl.

Among these compounds, there are more particularly preferred those in which:

$R^1$ and $R^2$, which may be identical or different, are each hydrogen, a $C_1$-$C_{20}$ alkyl radical, a $C_1$-$C_{20}$ alkoxy radical, a water-solubilizing substituent selected from among a carboxylate group, a sulfonate group or an ammonium residue;

$R^3$ is a group $COOR^5$, $COR^5$, $CONR^5R^6$;

$R^4$ is a group $COOR^6$, $COR^6$, $CONR^5R^6$; and the radicals $R^5$ and $R^6$, which may be identical or different, are each hydrogen, a $C_1$-$C_{12}$ alkyl radical, a $C_3$-$C_6$ cycloalkyl radical, a $C_3$-$C_{10}$ cycloalkenyl radical, a $C_7$-$C_{10}$ bicycloalkyl radical, a $C_3$-$C_{10}$ bicycloalkenyl radical, optionally substituted phenyl or naphthyl.

According to a particularly preferred embodiment, the compounds of formula (I) are selected from among those of the following formula (I'):

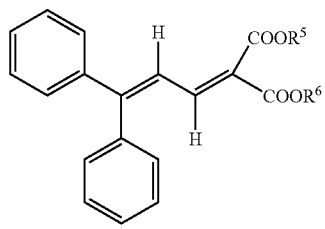
(I')

wherein the radicals $R^5$ and $R^6$, which may be identical or different, are each hydrogen, a $C_1$-$C_{20}$ alkyl radical, a $C_3$-$C_6$ cycloalkyl radical, a $C_3$-$C_{10}$ cycloalkenyl radical.

Among these compounds of formula (I'), there may be mentioned, more particularly, 1,1-dicarboxy(2',2'-dimethylpropyl)-4,4-diphenylbutadiene having the structure:

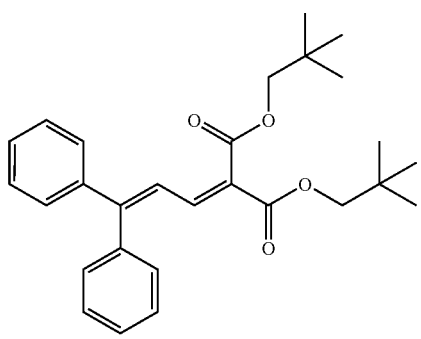
(compound f)

Another 4,4-diarylbutadiene family which may be formulated into the emulsions according to the invention are those corresponding to the following formula (II):

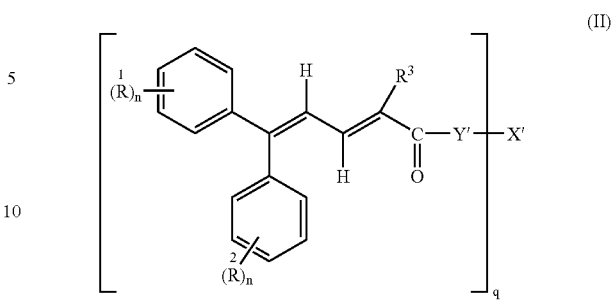
(II)

in which the diene system is of the Z,Z; Z,E; E,Z or E,E configuration or mixtures of the said configurations and wherein:

$R^1$, $R^2$, $R^3$ and $n$ have the same meanings indicated in the preceding formula (I);

Y' is a group —O— or —$NR^9$—;

$R^9$ is hydrogen, a linear or branched $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an aryl radical, a heteroaryl radical;

X' is a residue of a linear or branched, aliphatic or cycloaliphatic C2-C20 polyol comprising from 2 to 10 hydroxyl groups and having the valency q; with the proviso that the carbon chain of the said residue may be interrupted by one or more sulfur or oxygen atoms, one or more imine groups, one or more $C_1$-$C_4$ alkylimino groups; and q ranges from 2 to 10.

X' is a C2-C20 polyol residue containing from 2 to 10 hydroxyl groups, and in particular:

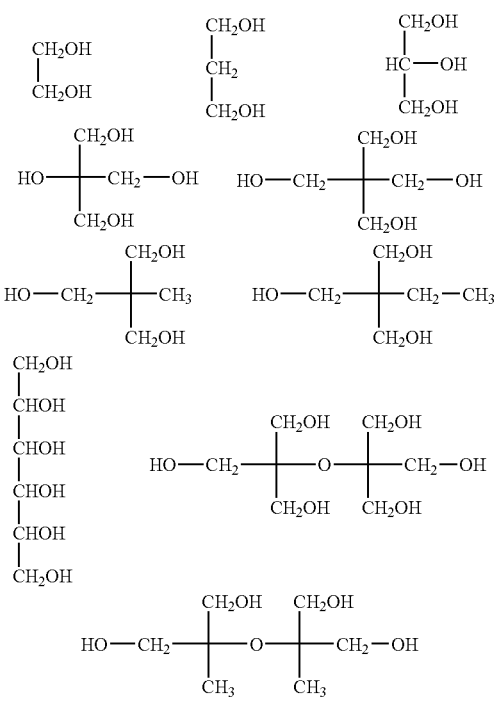

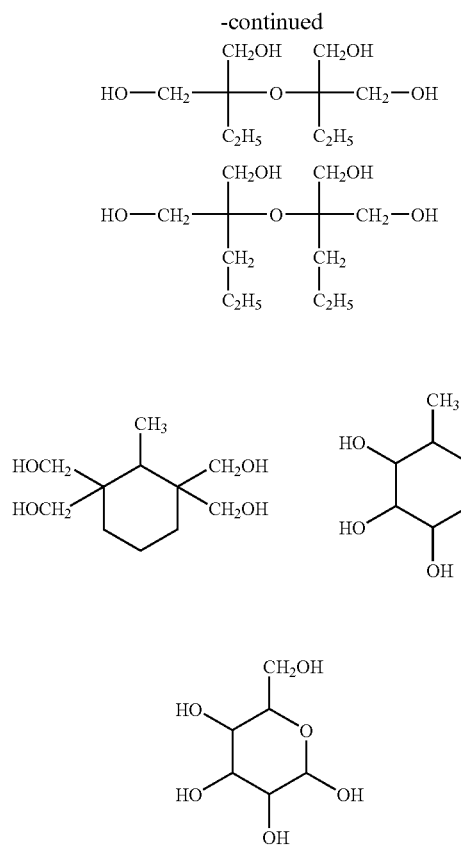

The more preferred compounds of formula (II) are those in which: $R^1$ and $R^2$, which may be identical or different, are each hydrogen, a $C_1$-$C_{12}$ alkyl radical, a $C_1$-$C_8$ alkoxy radical, a water-solubilizing substituent selected from among a carboxylate group, a sulfonate group or an ammonium residue;

$R^3$ is a group $COOR^5$, $CONR^5R^6$, CN, a $C_3$-$C_{10}$ cycloalkyl radical, a $C_7$-$C_{10}$ bicycloalkyl radical;

$R^5$ and $R^6$, which may be identical or different, are each a linear or branched $C_1$-$C_{20}$ alkyl radical, a $C_3$-$C_{10}$ cycloalkyl radical, a $C_7$-$C_{10}$ bicycloalkyl radical, optionally substituted naphthyl or phenyl; and X' is a C2-C20 polyol residue comprising from 2 to 6 hydroxyl groups and more particularly from 2 to 4.

The still more preferred compounds of formula (II) are those in which:

X' is an ethanol or pentaerythritol residue.

The even more particularly preferred compounds of formula (II) are selected from among:

The compounds of formula (II) as defined above are known per se and their structures and their syntheses are described in EP-A-1-008,586.

The 4,4-diarylbutadiene compounds are preferably present in the composition in proportions ranging from 0.1% to 20% by weight, more preferably from 1% to 10% by weight relative to the total weight of the composition.

According to a particular embodiment of the invention, the oil-in-water or water-in-oil emulsions prepared with the ionic polymer particles according to the invention may contain only 1% by weight or less, and may even be free of emulsifying surfactants, while being stable during storage.

The nature of the fatty phase comprising the composition of the emulsions according to the invention is not critical and it may thus comprise all the compounds which are already known in general as being suitable for the manufacture of water-in-oil type emulsions. In particular, these compounds may be selected, alone or as mixtures, from among various fatty substances, oils of plant, animal or mineral origin, natural or synthetic waxes, and the like.

Among the oils which may be formulated into the composition of the fatty phase, there may be mentioned in particular:

mineral oils such as paraffin oil and liquid paraffin, oils of animal origin, such as perhydrosqualene, oils of plant origin, such as sweet almond oil, avocado oil, castor oil, olive oil, jojoba oil, sesame oil, groundnut oil, grape seed oil, rapeseed oil, copra oil, hazelnut oil, shea butter, palm oil, apricot kernel oil, calophyllum oil, rice bran oil, maize germ oil, wheat germ oil, soya bean oil, sunflower oil, evening primrose oil, safflower oil, passion flower oil and rye oil, synthetic oils, such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and esters derived from lanolic acid such as isopropyl lanolate, isocetyl lanolate, isoparaffins and poly-α-olefins.

As other oils which can be formulated into the emulsions according to the invention, there may also be mentioned C12-C15 fatty alcohol benzoates (Finsolv TN from FINE-TEX), fatty alcohols such as lauryl, cetyl, myristyl, stearyl, palmityl or oleyl alcohol and 2-octyldodecanol, acetylglycerides, octanoates and decanoates of alcohols and polyalcohols such as those of glycol and of glycerol, ricinoleates of alcohols and polyalcohols such as those of cetyl, fatty acid triglycerides such as caprylic/capric triglycerides, C10-C18 saturated fatty acid triglycerides, fluorinated and perfluorinated oils, lanolin, hydrogenated lanolin, acetylated lanolin and finally volatile or nonvolatile silicone oils.

The oily phase of the emulsion may represent from 0.1% to 45% and better still from 5% to 30% of the total weight of the emulsion.

Of course, the fatty phase may also contain one or more conventional lipophilic cosmetic adjuvants, in particular those which are already customarily used in the manufacture and production of anti-sun cosmetic compositions.

Conventionally, the dispersive aqueous phase may comprise water, or a mixture of water and polyhydric alcohol(s) such as for example glycerol, propylene glycol and sorbitol, or alternatively a mixture of water and water-soluble lower alcohol(s) such as ethanol, isopropanol or butanol (aqueous-alcoholic solution), and it may of course additionally contain conventional water-soluble cosmetic adjuvants.

The compositions in accordance with the invention may further comprise other additional organic or inorganic UV-screening agents which are active in the UV-A and/or UV-B regions, which are water-soluble or fat-soluble or alternatively insoluble in the commonly-used cosmetic solvents.

The additional organic screening agents are selected, in particular, from among anthranilates; cinnamic derivatives; dibenzoylmethane derivatives; salicylic derivatives, camphor derivatives; triazine derivatives such as those described in U.S. Pat. No. 4,367,390, EP-863,145, EP-517,104, EP-570,838, EP-796,851, EP-775,698, EP-878,469, EP-933,376, EP-507,691, EP-507,692, EP-790,243 and EP-944,624; benzophenone derivatives; β,β'-diphenyl acrylate derivatives; benzotriazole derivatives; benzalmalonate derivatives; benzimidazole derivatives; imidazolines; bis-benzoazolyl derivatives as described in EP-669,323 and U.S. Pat. No. 2,463,264; p-aminobenzoic acid (PABA) derivatives; benzoxazole derivatives as described in EP-0, 832,642, EP-1,027,883, EP-1,300,137 and DE-1-0,162,844; methylenebis(hydroxyphenylbenzotriazole) derivatives as described in U.S. Pat. Nos. 5,237,071, 5,166,355, GB-2,303, 549, DE-1-9,726,184 and EP-893,119; screening polymers and screening silicones such as those described in particular in WO 93/04665; dimers derived from α-alkylstyrene such as those described in DE-1-9,855,649 and mixtures thereof.

As examples of organic screening agents which are active in the UV-A and/or UV-B regions, there may be mentioned those designated below under their INCI names:

para-Aminobenzoic Acid Derivatives:

PABA,

Ethyl PABA,

Ethyl Dihydroxypropyl PABA,

Ethylhexyl Dimethyl PABA sold in particular under the name "ESCALOL 507" by ISP, Glyceryl PABA, PEG-25 PABA sold under the name "UVINUL P25" by BASF, Salicylic Derivatives:

Homosalate sold under the name "Eusolex HMS" by Rona/EM Industries,

Ethylhexyl Salicylate sold under the name "NEO HELIOPAN OS" by Haarmann and REIMER, Dipropyleneglycol Salicylate sold under the name "DIPSAL" by SCHER, TEA Salicylate, sold under the name "NEO HELIOPAN TS" by Haarmann and REIMER, Dibenzoylmethane Derivatives:

Butyl Methoxydibenzoylmethane sold in particular under the trademark "PARSOL 1789" by HOFFMANN LA ROCHE, Isopropyl Dibenzoylmethane, Cinnamic Derivatives:

Ethylhexyl Methoxycinnamate sold in particular under the trademark "PARSOL MCX" by HOFFMANN LA ROCHE, Isopropyl Methoxy cinnamate, Isoamyl Methoxy cinnamate sold under the trademark "NEO HELIOPAN E 1000" by HAARMANN and REIMER, Cinoxate, DEA Methoxycinnamate, Diisopropyl Methylcinnamate, Glyceryl Ethylhexanoate Dimethoxycinnamate, ββ'-Diphenyl Acrylate Derivatives:

Octocrylene sold in particular under the trademark "UVINUL N539" by BASF,

Etocrylene, sold in particular under the trademark "UVINUL N35" by BASF,

Benzophenone Derivatives:

Benzophenone-1 sold under the trademark "UVINUL 400" by BASF,

Benzophenone-2 sold under the trademark "UVINUL D50" by BASF,

Benzophenone-3 or Oxybenzone, sold under the trademark "UVINUL M40" by BASF,

Benzophenone-4 sold under the trademark "UVINUL MS40" by BASF,

Benzophenone-5,

Benzophenone-6 sold under the trademark "Helisorb 11" by Norquay,

Benzophenone-8 sold under the trademark "Spectra-Sorb UV-24" by American Cyanamid, Benzophenone-9 sold under the trademark "UVINUL DS-49" by BASF, Benzophenone-12,
n-Hexyl 2-(4-diethylamino-2-hydroxybenzoyl)benzoate,
Benzylidenecamphor Derivatives:
3-Benzylidene camphor manufactured under the name "MEXORYL SD" by CHIMEX,
4-Methylbenzylidene camphor sold under the name "EUSOLEX 6300" by MERCK,
Benzylidene Camphor Sulfonic Acid manufactured under the name "MEXORYL SL" by CHIMEX,
Camphor Benzalkonium Methosulfate manufactured under the name "MEXORYL SO" by CHIMEX,
Terephthalylidene Dicamphor Sulfonic Acid manufactured under the name "MESORYL SX" by CHIMEX,
Polyacrylamidomethyl Benzylidene Camphor manufactured under the name "MESORYL SW" by CHIMEX,
Benzimidazole Derivatives:
Phenylbenzimidazole Sulfonic Acid sold in particular under the trademark "EUSOLEX 232" by MERCK,
Disodium Phenyl Dibenzimidazole Tetra-sulfonate sold under the trademark "NEO HELIOPAN AP" by Haarmann and REIMER,
Triazine Derivatives:
Anisotriazine sold under the trademark "TINOSORB S" by CIBA SPECIALTY CHEMICALS,
Ethylhexyl triazone sold in particular under the trademark "UVINUL T150" by BASF,
Diethylhexyl Butamido Triazone sold under the trademark "UV-ASORB HEB" by SIGMA 3V,
2,4,6-Tris(diisobutyl 4'-aminobenzalmalonate)-s-triazine,
Benzotriazole Derivatives:
Drometrizole Trisiloxane sold under the name "Silatrizole" by RHODIA CHIMIE,
Methylene bis-Benzotriazolyl Tetramethylbutylphenol, sold in solid form under the trademark "MIXXIM BB/100" by FAIRMOUNT CHEMICAL or in micronized form in aqueous dispersion under the trademark "TINOSORB M" by CIBA SPECIALTY CHEMICALS,
Anthranilic Derivatives:
Menthyl anthranilate sold under the trademark "NEO HELIOPAN MA" by Haarmann and REIMER,
Imidazoline Derivatives:
Ethylhexyl Dimethoxybenzylidene Dioxoimidazoline Propionate,
Benzalmalonate Derivatives:
Polyorganosiloxane with benzalmalonate functional groups such as polysilicone-15 sold under the trademark "PARSOL SLX" by HOFFMANN LAROCHE
Benzoxazole Derivatives:
2,4-Bis[5-1-(dimethylpropyl)benzoxazol-2-yl-(4-phenyl)imino]-6-(2-ethylhexy)imino-1,3,5-triazine sold under the name UV-Asorb K2A by Sigma 3V; and mixtures thereof.

The organic screening agents which are more particularly preferred are selected from among the following compounds:
Ethylhexyl Salicylate,
Ethylhexyl Methoxycinnamate,
Octocrylene,
Butyl Methoxydibenzoylmethane,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulfonic Acid,
Disodium Phenyl Dibenzimidazole Tetra-sulfonate,
2,4,6-Tris(diisobutyl 4'-aminobenzalmalonate)-s-triazine,
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone 15,
2,4-Bis-[5-1-(dimethylpropyl)benzoxazol-2-yl-(4-phenyl)imino]-6-(2-ethylhexyl)imino-1,3,5-triazine
and mixtures thereof.

The additional inorganic screening agents are selected from among pigments or nanopigments (average size of the primary particles: generally between 5 nm and 100 nm, preferably between 10 nm and 50 nm) of coated or uncoated metal oxides such as, for example, nanopigments of titanium oxide (amorphous or crystallized in rutile and/or anatase form), iron oxide, zinc oxide, zirconium oxide or cerium oxide which are all UV photoprotective agents well known per se. Conventional coating agents are moreover alumina and/or aluminum stearate. Such nanopigments of metal oxides, coated or uncoated, are described in particular in EP-518,772 and EP-518,773.

The additional screening agents according to the invention are generally present in the compositions according to the invention in an amount ranging from 0.1% to 30% by weight, and preferably from 0.5% to 15% by weight, relative to the total weight of the composition.

The compositions according to the invention may also contain agents for artificially bronzing and/or tanning the skin (self-tanning agents).

The self-tanning agents are generally selected from among mono- or polycarbonylated compounds such as for example isatin, alloxan, ninhydrin, glyceraldehyde, mesotartaric aldehyde, glutaraldehyde, erythrulose, derivatives of 4,5-pyrazolindiones as described in FR-2,466,492 and WO 97/35842, dihydroxyacetone (DHA), 4,4-dihydroxypyrazolin-5-one derivatives as described in EP-903,342. DHA will preferably be used.

DHA may be used in free form and/or encapsulated for example into lipid vesicles such as liposomes, which are described in particular in WO 97/25970.

The mono- or polycarbonylated self-tanning agents are generally present in the compositions according to the invention in proportions ranging from 0.1% to 10% by weight relative to the total weight of the composition, and preferably from 0.2% to 8% by weight relative to the total weight of the composition.

The compositions in accordance with the present invention may additionally comprise conventional cosmetic adjuvants, selected, in particular, from among organic solvents, ionic or nonionic thickeners and/or gelling agents, demulcents, humectants, opacifying agents, stabilizers, emollients, silicones, insect repellents, perfumes, preservatives, surfactants, fillers, pigments, polymers, propellants, alkanizing or acidifying agents or any other ingredient customarily used in the cosmetic and/or dermatological field.

Of course, one skilled in this art will be careful to choose the possible additional compound(s) cited above and/or their quantities such that the advantageous properties intrinsically attached to the emulsions in accordance with the invention are not, or not substantially, impaired by the addition(s) envisaged.

Among the organic solvents lower alcohols and polyols may be mentioned.

If it is desired to obtain a less fluid emulsion and/or to improve its cosmetic feel, it is possible to add one or more gelling agents thereto. These gelling agents are used in concentrations ranging from 0.1% to 10%, preferably 0.1% to 5% and better still from 0.1% to 3% of the total weight of the composition.

As gelling agents, exemplary are water-soluble or water-dispersible nonionic or anionic associative polymers having amphiphilic properties, containing at least one hydrophobic sequence and at least one hydrophilic sequence.

Water-soluble or Water-dispersible Nonionic Associative Polymers:

The hydrophobic sequence(s) are mainly fatty chains having from 6 to 30 carbon atoms, in particular hydrocarbon chains such as alkyl, aryl($C_1$-$C_8$)alkyl, ($C_1$-$C_8$)alkylaryl, alkenyl, aliphatic divalent groups such as $C_6$-$C_{30}$ alkylene, cycloaliphatic divalent groups such as in particular methylenedicyclohexyl, isophorone or aromatic divalent groups such as phenylene. The aryl radicals preferably are each phenyl, naphthyl or anthryl groups.

The hydrophilic sequence(s) may be, inter alia, a polyethylene oxide, a polysaccharide, a polyamide, in particular polyacrylamide, a polyester and mixtures thereof, and preferably a polyethylene oxide having from 15 to 500 ethylene oxides. The bond(s) between the hydrophobic and hydrophilic sequence is most often, without limitation, of the ester, ether, urea, amide or urethane type, and mixtures thereof.

The ratio (by weight) of the hydrophilic sequence(s) to the hydrophobic sequence(s) of the polymer is preferably between 10/1 and 1,000/1.

The water-soluble or water-dispersible nonionic associative polymers are preferably selected from among:

(1) Celluloses modified with groups containing at least one hydrophobic chain, for example:
hydroxyethylcelluloses modified with groups containing at least one fatty chain such as alkyl, arylalkyl, alkylaryl or alkenyl groups, or mixtures thereof, and in which the alkyl or alkenyl groups are preferably $C_8$-$C_{22}$, such as the product NATROSOL PLUS GRADE 330 CS ($C_{16}$ alkyls) sold by AQUALON, or the product BERMOCOLL EHM100 sold by BEROL NOBEL,
those modified with polyalkylene glycol ether groups of ($C_6$-$C_{20}$)alkylphenol, such as the product AMERCELL POLYMER HM-1500 (polyethylene glycol(15) ether of nonylphenol) sold by AMERCHOL;

(2) Hydroxypropylguars modified with groups containing at least one $C_{10}$-$C_{30}$ fatty chain such as the product ESAFLOR HM 22 ($C_{22}$ alkyl chain) sold by LAMBERTI, the products MIRACARE XC95-3 ($C_{14}$ alkyl chain) and RE205-1 ($C_{20}$ alkyl chain) sold by RHODIA CHIMIE;

(3) Polyether urethanes containing, in their chain, both hydrophilic sequences most often of a polyoxyethylenated nature and hydrophobic sequences which may be aliphatic linkages alone and/or cycloaliphatic and/or aromatic linkages.

Preferably, the polyether-polyurethanes contain at least two lipophilic hydrocarbon chains having from $C_6$ to $C_{30}$ carbon atoms, separated by a hydrophilic sequence, the hydrocarbon chains may be pendent chains or chains at the end of a hydrophilic sequence. In particular, it is possible for one or more pendent chains to be provided. In addition, the polymer may contain a hydrocarbon chain at one or at both ends of a hydrophilic sequence.

The polyether-polyurethanes may be multiblock, in particular in the form of a triblock. The hydrophobic sequences may be at each end of the chain (for example: triblock copolymer with a hydrophilic central sequence) or distributed both at the ends and in the chain (multiblock copolymer for example). These same polymers may also be graft or star-shaped units.

Preferably, the nonionic polyether-polyurethanes are triblock copolymers whose hydrophilic sequence contains at least one polyoxyethylenated chain containing from 50 to 1,000 oxyethylenated groups. The nonionic polyether-polyurethanes polyurethanes contain a urethane bond between the hydrophilic sequences, hence the origin of the name.

By implication, also included among the nonionic polyether-polyurethanes are those whose hydrophilic sequences are linked by other chemical bonds to the lipophilic sequences.

By way of examples of nonionic associative polyether-polyurethanes which can be used in the invention, there may be mentioned the polymer SER-AD FX1100 sold by SERVO DELDEN, a molecule containing an oxyethylenated unit and two $C_{18}$ hydrocarbon groups at the chain end linked to the ethylene oxide via a polyurethane sequence. As polymer, there may also be used Rheolate 205 with a urea functional group sold by RHEOX or alternatively Rheolate 208, 204 or 212; and Acrysol RM 184 from ROHM & HAAS;

(4) Copolymers of vinylpyrrolidone and hydrophobic monomers with a fatty chain, for example:
the products ANTARON V216 or GANEX V216 (vinylpyrrolidone/hexadecene copolymer) sold by I.S.P.;
the products ANTARON V220 or GANEX V220 (vinylpyrrolidone/eicosene copolymer) sold by I.S.P;

(5) Copolymers of $C_1$-$C_6$ alkyl methacrylates or acrylates and amphiphilic monomers containing at least one fatty chain such as for example the oxyethylenated methyl methacrylate/stearyl acrylate copolymer sold by GOLDSCHMIDT under the name ANTIL 208; and (6) Copolymers of hydrophilic methacrylates or acrylates and hydrophobic monomers containing at least one fatty chain such as for example the polyethylene glycol methacrylate/lauryl methacrylate copolymer.

Anionic Associative Polymers:

They are in general soluble in water at a pH greater than 3.5. They contain at least one hydrophobic chain, they are noncrosslinked and they preferably have a molecular weight ranging from 10,000 to 2,000,000. These polymers make it possible to increase the viscosity of the fluid emulsions (5 cP) by at least a factor of 10.

The hydrophobic chain(s) of the anionic associative polymers used according to the invention are in particular saturated or unsaturated, linear or branched hydrocarbon chains having from 6 to 30 carbon atoms, such as alkyl, arylalkyl, alkylaryl, alkylene; cycloaliphatic divalent groups such as in particular methylenedicyclohexyl or isophorone; or aromatic divalent groups such as phenylene.

The anionic polymers used in the present invention are preferably selected from among acrylic or methacrylic acid copolymers containing a hydrophilic sequence and at least one hydrophobic sequence.

The expression "copolymers" is understood to mean both the copolymers obtained from two sorts of monomers and those obtained from more than two sorts of monomers such as the terpolymers obtained from three sorts of monomers.

The anionic associative polymers preferably used in the invention are obtained by copolymerization of a monomer (a) selected from α-ethylenically unsaturated carboxylic acids (monomer a'), with a nonsurfactant ethylenically unsaturated monomer (b) different from (a) and/or an ethylenically unsaturated monomer (c) obtained from the reaction of an α-monoethylenically unsaturated acrylic monomer or a monoethylenically unsaturated isocyanate monomer with a monohydric nonionic amphiphilic component or with a primary or secondary fatty amine.

As anionic polymers containing at least one hydrophobic chain which may be used in the compositions of the invention, there may be mentioned in particular:

acrylic acid/ethyl acrylate/alkyl acrylate terpolymer, such as the product in the form of a 30% aqueous dispersion, marketed under the name Acusol 823 by Rohm & Haas;

acrylates/steareth-20 methacrylate copolymer such as the product marketed under the name Aculyn 22 by Rohm & Haas;

oxyethylenated (25 EO) (meth)acrylic acid/ethyl acrylate/behenyl methacrylate terpolymer, such as the product in the form of an aqueous emulsion, marketed under the name Aculyn 28 by Rohm & Haas;

oxyethylenated (20 EO) acrylic acid/monocetyl itaconate copolymer, such as the product in the form of a 30% aqueous dispersion, marketed under the name Structure 3001 by National Starch;

oxyethylenated (20 EO) acrylic acid/monostearyl itaconate copolymer such as the product in the form of a 30% aqueous dispersion, marketed under the name Structure 2001 by National Starch;

acrylates/acrylate copolymer modified with polyoxyethylenated (25 EO) $C_{12}$-$C_{24}$ alcohols, such as the latex containing 30%-32% copolymer, marketed under the name Synthalen W2000 by 3V SA;

ethoxylated methacrylic acid/methyl acrylate/dimethylmeta-isopropenyl benzyl isocyanate of behenyl alcohol terpolymer, such as the product in the form of a 24% aqueous dispersion and containing 40 oxyethylenated groups, described in EP-A-0,173,109.

The addition of neutralizing agents can prove useful for increasing the solubility of the polymers in water. It is then possible to use any known neutralizing agent, and in particular it is possible to select it from among the inorganic bases such as sodium hydroxide, potassium hydroxide, ammonia, and among the organic bases such as mono-, di- and triethanolamine, aminomethylpropane-1,3-diol, N-methylglucamine, basic amino acids such as arginine and lysine, and mixtures thereof. The quantity of neutralizing agent depends on the polymer used and the other constituents of the formula. It may range for example from 0.01% to 5%, and better still from 0.05% to 5% of the total weight of the composition.

As gelling agents, there may be mentioned polymers which are water-soluble and completely free of hydrophobic chain, selected, for example, from among homopolymers and copolymers of ethylene oxide; polyvinyl alcohols; homopolymers and copolymers of vinylpyrrolidone; homopolymers and copolymers of vinylcaprolactam; homopolymers and copolymers of polyvinyl methyl ether; nonionic acrylic homopolymers and copolymers; $C_1$-$C_2$ alkyl celluloses and their derivatives, hydroxymethylpropylcellulose; $C_1$-$C_3$ alkylguar or $C_1$-$C_3$ hydroxyalkylguar.

There may also be mentioned as gelling agents: nanometric silicas of the Aerosil type, fatty alcohols such as stearyl, cetyl and behenyl alcohols, algal derivatives such as satia gum, natural gums such as tragacanth, clays, polysaccharide gums such as xanthan gum, synthetic polymers such as mixtures of polyvinylcarboxylic acids marketed under the name CARBOPOL by GOODRICH and the mixture of Na acrylate/acrylamide copolymers, marketed under the name HOSTACERIN PN 73 by HOECHST.

The compositions according to the invention find application in a large number of treatments, in particular cosmetic treatments, of the skin, the lips and the hair, including the scalp, in particular for the protection and/or care of the skin, the lips and/or the hair, and/or for making up the skin and/or the lips.

The present invention thus features the use of the subject compositions for the manufacture of products for the cosmetic treatment of the skin, the lips and the hair, including the scalp, in particular for the protection and/or care of the skin, the lips and/or the hair, and/or for making up the skin and/or the lips.

The cosmetic compositions according to the invention may for example be used as care and/or sun protection product for the face and/or the body having a liquid to semi-liquid consistency, such as milks, more or less unctuous creams, gel creams, pastes. They may be optionally packaged as an aerosol and may be provided in the form of a mousse or a spray.

The compositions according to the invention in the form of vaporizable fluid lotions in accordance with the invention are applied to the skin or the hair in the form of fine particles by means of pressurized devices. The devices in accordance with the invention are well known to persons skilled in the art and comprise nonaerosol pumps or "atomizers", the aerosol containers comprising a propellant and aerosol pumps using compressed air as propellant. The latter are described in U.S. Pat. Nos. 4,077,441 and 4,850,517.

The compositions packaged as an aerosol in accordance with the invention contain in general conventional propellants such as, for example, the hydrofluorinated compounds dichlorodifluoromethane, difluoroethane, dimethyl ether, isobutane, n-butane, propane, trichlorofluoromethane. They are preferably present in quantities ranging from 15% to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

| Phase A: | |
|---|---|
| AQ38S (Eastman Chemical) | 2.0% |
| Glycerin | 5.0% |
| Preservatives | 1.2% |
| Sequestrant | 0.1% |
| Demineralized water | 49.2% |
| Phase B: | |
| Liquid paraffin | 10.0% |
| Octyl methoxycinnamate | 7.0% |
| 1,1-Dicarboxy-(2',2'-dimethylpropyl)-4,4-diphenylbutadiene (compound f) | 5.0% |
| Octyldodecanol | 5.0% |
| $C_{12-15}$ alkyl benzoate | 15.0% |

The constituents of phase A are mixed and the mixture is heated to 70° C., with magnetic stirring, until complete dispersion of the polymer is obtained, then the solution is cooled to room temperature. Phase B is moreover prepared. Phase A is introduced into phase B, with vigorous stirring. The emulsion is homogenized at a pressure of 600 bar (2 to 4 passes), the emulsion being brought to room temperature between each pass. The size of the oil drops is of the order of 250 nm.

A sprayable stable fluid emulsion capable of protecting the skin against the sun's rays is obtained.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A fluid, homogenized, UV-photoprotective oil-in-water emulsion, microscopically and microscopically stable for a period of time of at least 30 days in the absence of phase separation, the oil globules of which having an average size of at most 500 nm, containing particles of at least one ionic polymer and at least one UV radiation-screening system, said screening system comprising at least one 4,4-diarylbutadiene UV-A-screening agent.

2. The oil-in-water emulsion as defined by claim 1, devoid of surfactant.

3. The oil-in-water emulsion as defined by claim 1, said at least one ionic polymer comprising an anionic or cationic polymer or mixture thereof, or a mixture of at least one ionic polymer and at least one nonionic polymer.

4. The oil-in-water emulsion as defined by claim 1, said at least one ionic polymer comprising an anionic polymer.

5. The oil-in-water emulsion as defined by claim 4, said at least one ionic polymer comprising a copolymer of isophthalic acid and/or sulfoisophthalic acid.

6. The oil-in-water emulsion as defined by claim 5, said at least one ionic polymer comprising a copolymer of phthalate/sulfoisophthalate/glycol.

7. The oil-in-water emulsion as defined by claim 6, said at least one ionic polymer comprising a copolymer of diethylene glycol/phthalate/isophthalate/1,4-cyclohexanedimethanol.

8. The oil-in-water emulsion as defined by claim 5, wherein the proportion of structural units derived from sulfoisophthalic acid ranges from 2% to 20% by weight relative to the total weight of the polymer.

9. The oil-in-water emulsion as defined by claim 1, comprising at least one water-dispersible ionic polymer which comprises a film-forming cosmetic vinyl copolymer.

10. The oil-in-water emulsion as defined by claim 9, said film-forming vinyl copolymer being selected from the group consisting of:
(i) polyethoxylated vinyl acetate/crotonic acid copolymers;
(ii) vinyl acetate/crotonic acid copolymers;
(iii) vinyl acetate/crotonic acid/vinyl neodecanoate terpolymers;
(iv) N-octylacrylamide/methyl methacrylate/hydroxypropyl methacrylate/acrylic acid/tert-butylaminoethyl methacrylate copolymers;
(v) methyl vinyl ether/maleic anhydride alternating copolymers monoesterified with butanol; and
(vi) acrylic acid/ethyl acrylate/N-tert-butylacrylamide terpolymers.

11. The oil-in-water emulsion as defined by claim 1, said at least one ionic polymer comprising a natural water-dispersible anionic polymer.

12. The oil-in-water emulsion as defined by claim 11, said natural water-dispersible anionic polymer comprising a shellac resin, sandarac gum or dammar.

13. The oil-in-water emulsion as defined by claim 1, comprising at least one water-dispersible ionic polymer having a weight-average molar mass ranging from 1,000 to 5,000,000.

14. The oil-in-water emulsion as defined by claim 1, comprising particles of at least one water-dispersible ionic polymer having a particle size ranging from 10 to 400 nanometers.

15. The oil-in-water emulsion as defined by claim 1, the particles of said at least one ionic polymer constituting from 0.1% to 10% of the total weight of the emulsion.

16. The oil-in-water emulsion as defined by claim 1, the weight ratio of the particles of said at least one ionic polymer to the oily phase ranging from 1/5 to 1/40.

17. The oil-in-water emulsion as defined by claim 1, the oily phase constituting from 0.1% to 45% of the total weight of the emulsion.

18. The oil-in-water emulsion as defined by claim 1, said at least one 4,4-diarylbutadiene UV-A-screening agent having the following formula (I):

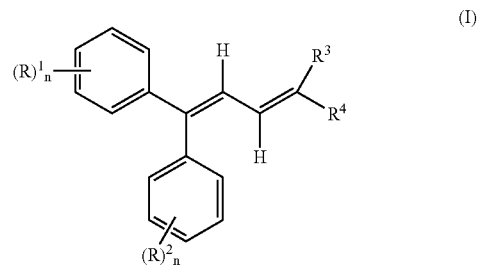

in which the diene system is of the Z,Z; Z,E; E,Z or E,E configuration or mixture of said configurations, and wherein:

$R^1$ and $R^2$, which may be identical or different, are each hydrogen, a $C_1$-$C_{20}$ alkyl radical, a $C_2$-$C_{10}$ alkenyl radical, a $C_1$-$C_{12}$ alkoxy radical, a $C_3$-$C_{10}$ cycloalkyl radical, a $C_3$-$C_{10}$ cycloalkenyl radical, a $C_1$-$C_{20}$ alkoxycarbonyl radical, a $C_1$-$C_{12}$ monoalkylamino radical, a $C_1$-$C_{12}$ dialkylamino radical, an aryl radical, a heteroaryl radical or a water-solubilizing substituent selected from among a carboxylate residue, a sulfonate residue or an ammonium residue;

$R^3$ is a group $COOR^5$, $COR^5$, $CONR^5R^6$, CN, O=S(—$R^5$)=O, O=S(—$OR^5$)=O, $R^7O$—P—(—$OR^8$)=O, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$C_8$ aryl radical, an optionally substituted $C_3$-$C_7$ heteroaryl radical;

$R^4$ is a group $COOR^6$, $COR^6$, $CONR^5R^6$, CN, O=S(—$R^6$)=O, O=S(—$OR^6$)=O, $R^7O$—P—(—$OR^8$)=O, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$Ci8$ aryl radical, an optionally substituted $C_3$-$C_7$ heteroaryl radical;

the radicals $R^5$ to $R^8$, which may be identical or different, are each hydrogen, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ bicycloalkenyl radical, a $C_7-C_{10}$ cycloalkenyl radical, an optionally substituted aryl radical, an optionally substituted heteroaryl radical;

n ranges from 1 to 3; with the proviso that the radicals $R^3$ to $R^8$ can together form, with the carbon atoms from which they depend, a $C_5-C_6$ ring which may be fused.

19. The oil-in-water emulsion as defined by claim 18, wherein said compound of formula (I):

n=1 or 2;

$R^1$ and $R^2$, which may be identical or different, are each hydrogen, a $C_1-C_{20}$ alkyl radical, a $C_1-C_{12}$ alkoxy radical, a $C_1-C_{12}$ monoalkylamino radical, a $C_1-C_{12}$ dialkylamino radical, a water-solubilizing substituent selected from among a carboxylate group, a sulfonate group or an ammonium residue;

$R^3$ is a group $COOR^5$, $COR^5$, $CONR^5R^6$, a $C_1-C_{20}$ alkyl radical, a $C_3-C_{10}$ cycloalkyl radical, a $C_3-C_{10}$ cycloalkenyl radical, a $C_7-C_{10}$ bicycloalkyl radical, optionally substituted phenyl, naphthyl or thienyl;

$R^4$ is a group $COOR^6$, $COR^6$, $CONR^5R^6$, a $C_1-C_{20}$ alkyl radical, a $C_3-C_6$ cycloalkyl radical, a $C_3-C_{10}$ cycloalkenyl radical, a $C_7-C_{10}$ bicycloalkyl radical, optionally substituted phenyl, naphthyl or thienyl;

the radicals $R^5$ and $R^6$, which may be identical or different, are each hydrogen, a $C_1-C_{12}$ alkyl radical, a $C_3-C_{10}$ cycloalkyl radical, a $C_3-C_{10}$ cycloalkenyl radical, a $C_7-C_{10}$ bicycloalkyl radical, a $C_3-C_{10}$ bicycloalkenyl radical, optionally substituted phenyl or naphthyl.

20. The oil-in-water emulsion as defined by claim 19, wherein said compound of formula (I):

$R^1$ and $R^2$, which may be identical or different, are each hydrogen, a $C_1-C_{20}$ alkyl radical, a $C_1-C_{20}$ alkoxy radical, a water-solubilizing substituent selected from among a carboxylate group, a sulfonate group or an ammonium residue;

$R^3$ is a group $COOR^5$, $COR^5$, $CONR^5R^6$;

$R^4$ is a group $COOR^6$, $COR^6$, $CONR^5R^6$;

the radicals $R^5$ and $R^6$, which may be identical or different, are each hydrogen, a $C_1-C_{12}$ alkyl radical, a $C_3-C_6$ cycloalkyl radical, a $C_3-C_{10}$ cycloalkenyl radical, a $C_7-C_{10}$ bicycloalkyl radical, a $C_3-C_{10}$ bicycloalkenyl radical, optionally substituted phenyl or naphthyl.

21. The oil-in-water emulsion as defined by claim 20, said compound of formula (I) being selected from among those of the following formula (I'):

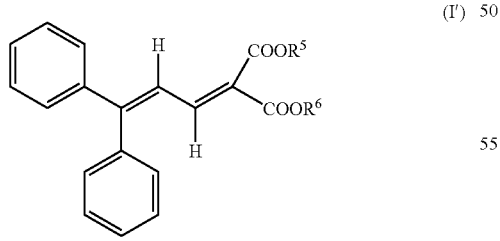

(I')

wherein the radicals $R^5$ and $R^6$, which may be identical or different, are each hydrogen, a $C_1-C_{20}$ alkyl radical, a $C_3-C_6$ cycloalkyl radical, a $C_3-C_{10}$ cycloalkenyl radical.

22. The oil-in-water emulsion as defined by claim 21, said compound of formula (I') comprising 1,1-dicarboxy(2',2'-dimethylpropyl)-4,4-diphenylbutadiene having the structure:

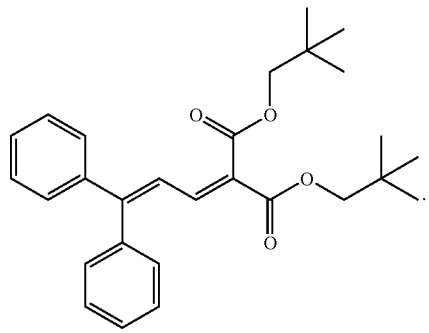

(compound f)

23. The oil-in-water emulsion as defined by claim 1, said at least one 4,4-diarylbutadiene UV-A screening agent having the following formula (II):

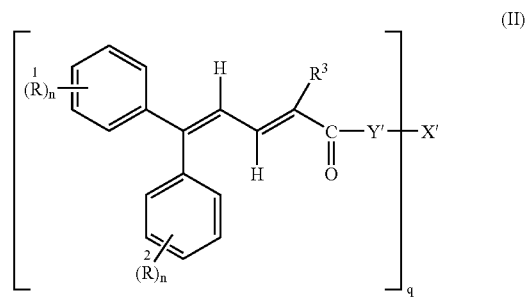

(II)

in which the diene system is of the Z,Z; Z,E; E,Z or E,E configuration or mixture of the said configurations and wherein:

$R^1$, $R^2$, $R^3$ and n have the meanings indicated in the formula (I);

Y' is a group —O— or —$NR^9$—;

$R^9$ is hydrogen, a linear or branched $C_1-C_{20}$ alkyl radical, a $C_2-C_{10}$ alkenyl radical, a $C_3-C_{10}$ cycloalkyl radical, a $C_7-C_{10}$ bicycloalkyl radical, a $C_3-C_{10}$ cycloalkenyl radical, a $C_7-C_{10}$ bicycloalkenyl radical, an aryl radical, a heteroaryl radical;

X' is a residue of a linear or branched, aliphatic or cycloaliphatic C2-C20 polyol comprising from 2 to 10 hydroxyl groups and having the valency q; with the proviso that the carbon chain of said residue may be interrupted by one or more sulfur or oxygen atoms, one or more imine groups, one or more $C_1-C_4$ alkylimino groups; and q ranges from 2 to 10.

24. The oil-in-water emulsion as defined by claim 23, wherein said compound of formula (II):

$R^1$ and $R^2$, which may be identical or different, are each hydrogen, a $C_1-C_{12}$ alkyl radical, a $C_1-C_8$ alkoxy radical, a water-solubilizing substituent selected from among a carboxylate group, a sulfonate group or an ammonium residue;

$R^3$ is a group $COOR^5$, $CONR^5R^6$, CN, a $C_3-C_{10}$ cycloalkyl radical, a $C_7-C_{10}$ bicycloalkyl radical;

$R^5$ and $R^6$, which may be identical or different, are each a linear or branched $C_1-C_{20}$ alkyl radical, a $C_3-C_{10}$ cycloalkyl radical, a $C_7-C_{10}$ bicycloalkyl radical, optionally substituted naphthyl or phenyl; and X' is a C2-C20 polyol residue comprising from 2 to 6 hydroxyl groups.

25. The oil-in-water emulsion as defined by claim 24, wherein said compound of formula (II), X' is an ethanol or pentaerythritol residue.

26. The oil-in-water emulsion as defined by claim 25, said at least one compound of formula (II) being selected from among the following compounds:

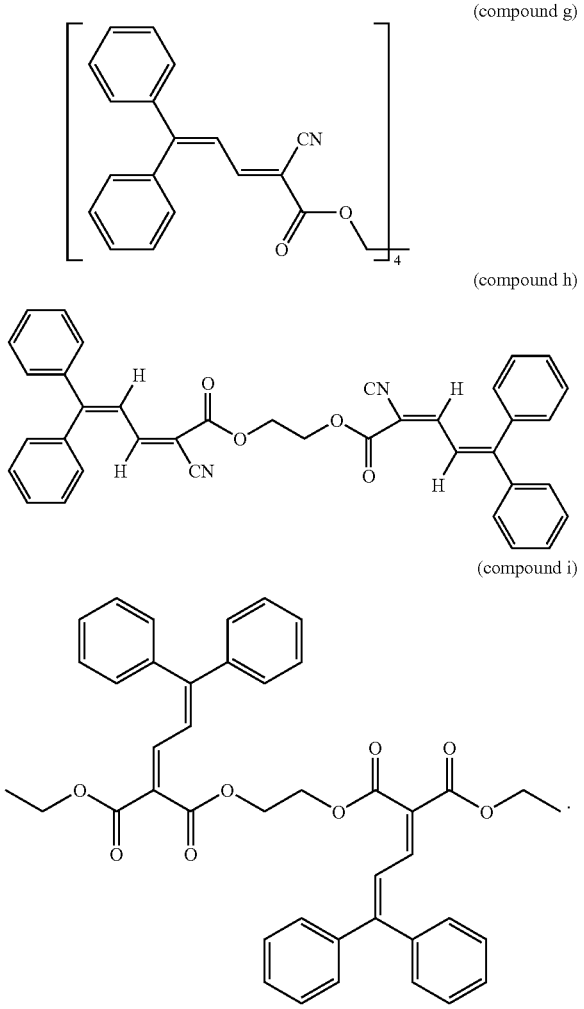

(compound g)

(compound h)

(compound i)

27. The oil-in-water emulsion as defined by claim 1, said at least one 4,4-diarylbutadiene UV-A screening agent constituting from 0.1% to 20% by weight relative to the total weight of the emulsion.

28. The oil-in-water emulsion as defined by claim 1, further comprising at least one additional organic or inorganic sunscreening agent active in the UV-A and/or UV-B regions, water-soluble, fat-soluble or insoluble in the usual cosmetic solvents.

29. The oil-in-water emulsion as defined by claim 28, comprising at least one additional organic screening agent selected from among the anthranilates; cinnamic derivatives; dibenzoylmethane derivatives; salicylic derivatives, camphor derivatives; triazine derivatives; benzophenone derivatives; β,β'-diphenyl acrylate derivatives; benzotriazole derivatives; benzalmalonate derivatives; benzimidazole derivatives; imidazolines; bis-benzoazolyl derivatives; p-aminobenzoic acid (PABA) derivatives; benzoxazole derivatives; methylenebis(hydroxyphenylbenzotriazole) derivatives; screening polymers and screening silicones; dimers derived from α-alkylstyrene and mixtures thereof.

30. The oil-in-water emulsion as defined by claim 29, said at least one additional organic screening agent comprising:
Ethylhexyl Salicylate,
Ethylhexyl Methoxycinnamate,
Octocrylene,
Butyl Methoxydibenzoylmethane,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulfonic Acid,
Disodium Phenyl Dibenzimidazole Tetra-sulfonate,
2,4,6-Tris(4'-diisobutyl aminobenzalmalonate)-s-triazine
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone 15,
2,4-Bis-[5-1-(dimethylpropyl)benzoxazol-2-yl-(4-phenyl)imino]-6-(2-ethylhexyl)imino-1,3,5-triazine, or
mixture thereof.

31. The oil-in-water emulsion as defined by claim 28, comprising at least one additional inorganic screening agent selected from among pigments or nanopigments of metal oxides, coated or uncoated.

32. The oil-in-water emulsion as defined by claim 31, said at least one additional inorganic screening agent comprising nanopigments of titanium oxide, amorphous or crystallized, in rutile and/or anatase form, iron oxide, zinc oxide, zirconium oxide or cerium oxide.

33. The oil-in-water emulsion as defined by claim 1, further comprising at least one agent for artificial bronzing and/or tanning of the skin.

34. The oil-in-water emulsion as defined by claim 1, further comprising at least one cosmetic adjuvant selected from among organic solvents, ionic or nonionic thickeners and/or gelling agents, demulcents, humectants, opacifying agents, stabilizers, emollients, silicones, insect repellents, perfumes, preservatives, surfactants, fillers, pigments, polymers, propellants, alkalinizing or acidifying agents, or any other ingredient commonly employed in the cosmetic and/or dermatological field.

35. The oil-in-water emulsion as defined by claim 1, comprising at most 1% by weight of an emulsifying surfactant.

36. The oil-in-water emulsion as defined by claim 1, further comprising at least one gelling agent.

37. The oil-in-water emulsion as defined by claim 36, said at least one gelling agent constituting from 0.1% to 10% of the total weight of the emulsion.

38. The oil-in-water emulsion as defined by claim 36, said at least one gelling agent comprising a water-soluble or water-dispersible nonionic or anionic associative polymer containing at least one hydrophobic sequence and at least one hydrophilic sequence.

39. The oil-in-water emulsion as defined by claim 36, comprising at least one nonionic associative polymer selected from among:

(1) celluloses modified with groups containing at least one hydrophobic chain;
(2) hydroxypropylguars modified with groups containing at least one $C_{10}$-$C_{30}$ fatty chain;
(3) polyether urethanes containing, in their chain, both hydrophilic sequences and hydrophobic sequences which may be aliphatic linkages alone and/or cycloaliphatic and/or aromatic linkages;
(4) copolymers of vinylpyrrolidone and hydrophobic monomers with a fatty chain;
(5) copolymers of $C_1$-$C_6$ alkyl methacrylates or acrylates and amphiphilic monomers containing at least one fatty chain; and
(6) copolymers of hydrophilic methacrylates or acrylates and hydrophobic monomers containing at least one fatty chain.

40. The oil-in-water emulsion as defined by claim 38, comprising an anionic associative polymer selected from among copolymers of acrylic or methacrylic acid containing a hydrophilic sequence and at least one hydrophobic sequence.

41. The oil-in-water emulsion as defined by claim 38, comprising an anionic associative polymer selected from among:
   acrylic acid/ethyl acrylate/alkyl acrylate terpolymer;
   acrylates/steareth-20 methacrylate copolymer;
   oxyethylenated (25 EO) (meth)acrylic acid/ethyl acrylate/behenyl methacrylate terpolymer;
   oxyethylenated (20 EO) acrylic acid/monocetyl itaconate copolymer;
   oxyethylenated (20 EO) acrylic acid/monostearyl itaconate copolymer;
   acrylates/acrylate copolymer modified with polyoxyethylenated (25 EO) $C_{12}$-$C_{24}$ alcohols;
   ethoxylated methacrylic acid/methyl acrylate/dimethyl-meta-isopropenyl benzyl isocyanate of behenyl alcohol terpolymer.

42. The oil-in-water emulsion as defined by claim 36, comprising at least one gelling agent selected from among water-soluble polymers devoid of a hydrophobic chain.

43. The oil-in-water emulsion as defined by claim 42, said polymers which are water-soluble and devoid of hydrophobic chain being selected from among homopolymers and copolymers of ethylene oxide; polyvinyl alcohols; homopolymers and copolymers of vinylpyrrolidone; homopolymers and copolymers of vinylcaprolactam; homopolymers and copolymers of polyvinyl methyl ether; nonionic acrylic homopolymers and copolymers; $C_1$-$C_2$ alkyl celluloses and derivatives thereof, hydroxymethylpropylcellulose; $C_1$-$C_3$ alkylguar or $C_1$-$C_3$ hydroxyalkylguar.

44. The oil-in-water emulsion as defined by claim 36, said at least one gelling agent being selected from among nanometric silicas, fatty alcohols, algal derivatives, natural gums, tragacanth, clays, polysaccharide gums and synthetic polymers.

45. A method of formulating an emulsion as defined by claim 1, comprising first mixing, with stirring, the aqueous phase, the oily phase and the polymer particles and then subjecting the mixture obtained to homogenization via cavitation.

46. The method as defined by claim 45, the homogenization being carried out at a pressure ranging from 400 to 700 bar.

47. A method for the photoprotection of the skin, lips and/or hair against the damaging effects of UV radiation, comprising topically applying thereon a thus effective amount of a fluid, homogenized, UV-photoprotective oil-in-water emulsion, microscopically and microscopically stable for a period of time of at least 30 days in the absence of phase separation, the oil globules of which having an average size of at most 500 nm, containing particles of at least one ionic polymer and at least one UV radiation-screening system, said screening system comprising at least one 4,4-diarylbutadiene UV-A-screening agent.

* * * * *